United States Patent [19]
Draenert

[11] Patent Number: 5,993,716
[45] Date of Patent: *Nov. 30, 1999

[54] MATERIAL AND PROCESS FOR ITS PREPARATION

[76] Inventor: Klaus Draenert, Gabriel-Max-Strasse 3, München, Germany, D-81545

[*] Notice: This patent is subject to a terminal disclaimer.

[21] Appl. No.: 08/990,058

[22] Filed: Dec. 12, 1997

Related U.S. Application Data

[62] Continuation-in-part of application No. 08/619,266, Mar. 18, 1996, abandoned, and application No. 08/407,395, Mar. 17, 1995, Pat. No. 5,746,200, said application No. 08/619,266, is a continuation of application No. 08/415,205, Mar. 31, 1995, abandoned, which is a continuation of application No. 08/039,360, filed as application No. PCT/EP91/01997, Oct. 21, 1991, abandoned, said application No. 08/407,395, is a continuation of application No. 07/862,741, filed as application No. PCT/EP91/01998, Oct. 21, 1991, abandoned.

[30] Foreign Application Priority Data

Oct. 19, 1990 [DE] Germany ............................ 40 33 291
Oct. 19, 1990 [DE] Germany ............................ 40 33 344

[51] Int. Cl.⁶ .................. B29C 33/54; A61F 2/28
[52] U.S. Cl. ............ 264/221; 428/131; 428/304.4; 428/312.2; 428/313.3; 428/338; 428/323; 623/16; 623/901; 424/423; 264/49; 264/317; 264/DIG. 44; 264/220; 264/222; 264/223; 264/224; 264/225; 264/227; 264/226; 264/219
[58] Field of Search ................... 428/131, 304.4, 428/312.2, 313.3, 338, 323; 623/16, 901; 424/423; 264/49, 317, DIG. 44, 220, 221, 222, 223, 224, 225, 227, 226, 219

[56] References Cited

U.S. PATENT DOCUMENTS

| | | | |
|---|---|---|---|
| 1,322,375 | 11/1919 | Un | 128/206.11 |
| 2,057,397 | 10/1936 | Strauch | 128/206.11 |
| 2,097,846 | 11/1937 | Strauch | 128/206.11 |
| 2,162,583 | 6/1939 | Kjelvon | 128/206.11 |
| 2,340,223 | 1/1944 | Krill | 128/206.11 |
| 3,476,844 | 11/1969 | Villain | 128/206.11 |
| 3,513,839 | 5/1970 | Vacante | 128/206.11 |
| 3,766,000 | 10/1973 | Gibson et al. | 161/170 |
| 3,789,029 | 1/1974 | Hodosh | 260/2.5 |
| 3,852,045 | 12/1974 | Wheeler et al. | 29/182 |
| 3,890,107 | 6/1975 | White et al. | 156/58 |
| 3,899,556 | 8/1975 | Heide et al. | 264/44 |
| 3,905,335 | 9/1975 | Kapp | 128/206.11 |
| 4,007,494 | 2/1977 | Sauer | 3/1.9 |
| 4,093,576 | 6/1978 | deWijn | 260/17 |
| 4,131,597 | 12/1978 | Bluethgen et al. | 260/42.18 |
| 4,141,864 | 2/1979 | Rijke et al. | 260/17.4 |
| 4,177,524 | 12/1979 | Grell et al. | 3/1.9 |
| 4,192,021 | 3/1980 | Deibig et al. | 3/1.9 |
| 4,221,217 | 9/1980 | Amezcua | 128/206.11 |
| 4,231,120 | 11/1980 | Day | 3/1.91 |
| 4,245,359 | 1/1981 | Stuhmer | 3/1.91 |
| 4,259,072 | 3/1981 | Hirabayashi et al. | 3/1.9 |
| 4,267,831 | 5/1981 | Aquilar | 128/206.11 |
| 4,371,484 | 2/1983 | Inukai et al. | 264/44 |
| 4,373,217 | 2/1983 | Draenert | 3/1.9 |
| 4,383,956 | 5/1983 | Croft et al. | 264/49 |
| 4,401,117 | 8/1983 | Gershuny | 128/206.11 |
| 4,500,658 | 2/1985 | Fox | 523/117 |
| 4,547,390 | 10/1985 | Ashman et al. | 427/2 |
| 4,629,464 | 12/1986 | Takata et al. | 623/16 |
| 4,644,942 | 2/1987 | Sump | 623/16 |
| 4,645,503 | 2/1987 | Lin et al. | 623/16 |
| 4,652,593 | 3/1987 | Kawahara et al. | 523/116 |
| 4,671,263 | 6/1987 | Draenert | 128/92 |
| 4,686,973 | 8/1987 | Frisch | 128/92 |
| 4,718,910 | 1/1988 | Draenert | 623/16 |
| 4,722,870 | 2/1988 | White | 428/621 |
| 4,781,721 | 11/1988 | Grundei | 623/16 |
| 4,839,215 | 6/1989 | Starling et al. | 428/131 |
| 4,853,225 | 8/1989 | Wahlig et al. | 424/423 |
| 4,859,712 | 8/1989 | Cox | 521/62 |
| 4,863,444 | 9/1989 | Blömer | 604/304 |

(List continued on next page.)

FOREIGN PATENT DOCUMENTS

| | | |
|---|---|---|
| 0 041 614 | 12/1981 | European Pat. Off. |
| 0 047 971 | 3/1982 | European Pat. Off. |
| 0 107 476 | 10/1983 | European Pat. Off. |
| 0 177 781 | 4/1986 | European Pat. Off. |
| 0 276 836 | 1/1988 | European Pat. Off. |
| 0 277 678 | 1/1988 | European Pat. Off. |
| 0 338981 | 4/1989 | European Pat. Off. |
| 0 332 371 | 9/1989 | European Pat. Off. |
| 530680 | 10/1957 | France . |
| 1395197 | 3/1965 | France . |
| 1402857 | 5/1965 | France . |
| 2 344 280 | 10/1977 | France . |
| 1392000 | 2/1998 | France . |
| 2 242 867 | 8/1972 | Germany . |
| 2910627 | 4/1980 | Germany . |
| 29 05 878 | 8/1980 | Germany . |
| 3309855 | 3/1983 | Germany . |
| 3445 709 A1 | 12/1984 | Germany . |
| 3531144 | 8/1985 | Germany . |
| 60-179102 | 9/1985 | Japan . |
| 60-202703 | 10/1985 | Japan . |
| 908185 | 10/1960 | United Kingdom . |
| 2 093 701 | 9/1982 | United Kingdom . |
| 8900842 | 2/1984 | WIPO . |
| 8603671 | 12/1985 | WIPO . |
| WO 88/06023 | 8/1988 | WIPO . |
| WO 92/04924 | 4/1992 | WIPO . |

OTHER PUBLICATIONS

*Hawley's Condensed Chemical Dictionary*, 11ᵗʰ ed., Sax et al., 15BN0442280971 at 1987.

Primary Examiner—William P. Watkins, III
Attorney, Agent, or Firm—Kinney & Lange, P.A.

[57] ABSTRACT

The invention relates to a material of a three-dimensional framework of supporting, trabecular structures encompassing cavities which are connected with one another and which can be predeterminedly adjusted. The material is obtainable by forming the framework around the shaped bodies serving as space retainers for the cavities and subsequently removing the shaped bodies. The material according to the invention can be used for example as a implant or as a filter.

32 Claims, No Drawings

U.S. PATENT DOCUMENTS

| | | | |
|---|---|---|---|
| 4,891,182 | 1/1990 | Sakamoto et al. | 416/2 |
| 4,919,666 | 4/1990 | Buckhorn et al. | 623/16 |
| 4,950,295 | 8/1990 | Weigum et al. | 623/16 |
| 4,969,906 | 11/1990 | Kronman | 623/16 |
| 4,984,302 | 1/1991 | Lincoln | 128/206.11 |
| 4,999,157 | 3/1991 | Nishio et al. | 419/68 |
| 5,089,135 | 2/1992 | Yoneyama et al. | 210/500.23 |
| 5,089,186 | 2/1992 | Moore et al. | 264/25 |
| 5,096,814 | 3/1992 | Aivasidas et al. | 435/41 |
| 5,117,820 | 6/1992 | Robitaille | 128/206.11 |
| 5,201,766 | 4/1993 | Georgette | 623/16 |
| 5,266,248 | 11/1993 | Ohtsuka et al. | 264/44 |
| 5,276,070 | 1/1994 | Arroyo | 523/117 |
| 5,522,894 | 6/1996 | Draenert | 623/16 |
| 5,746,200 | 5/1998 | Draenert | 128/206.11 |

MATERIAL AND PROCESS FOR ITS PREPARATION

This application is a continuation-in-part of Ser. No. 08/619,266, filed Mar. 18, 1996, now abandoned, and a continuation-in-part of Ser. No. 08/407,395, filed Mar. 17, 1995, now U.S. Pat. No. 5,746,200, said Ser. No. 08/619,266, filed Mar. 18, 1996, now abandoned, is a continuation of Ser. No. 08/415,205, filed Mar. 31, 1995, now abandoned, which is a continuation of Ser. No. 08/039,360, filed Jun. 8, 1993, now abandoned, which is a 371 National Phase application of PCT/EP91/01997, filed Oct. 21, 1991, said Ser. No. 08/407,395, filed Mar. 17, 1995, now U.S. Pat. No. 5,746,200, is a continuation of Ser. No. 07/862,741, filed Jun. 19, 1992, now abandoned, which is a 371 National Phase application of PCT/EP91/01998, filed Oct. 21, 1991. Application Ser. No. 08/407,395 is incorporated by reference.

The invention relates to a material, a process for its preparation and its use.

There is a need generally and in particular in medicine for materials which offer maximum strength whilst providing a maximum reduction in the amount of required material and/or being lightweight. There is also a need, for example in filter technology, for materials having a structure with which it is possible on account of the continuous porosity of the material to absorb gases or liquids along large surfaces or to hold particles in an adjustable cavity system of the material.

A process for preparing an implant as a bone replacement in the form of an open pore or open cell shaped body of body compatible metal is known from DE-C2-31 06 917, wherein the metal is processed using a disposable pattern. In this process open pore or open cell natural or artificial sponges with an average pore or cell width of between 0.5 and 1.5 mm, which are filled with a ceramic embedding mass, are used as the positive pattern. The pattern material is subsequently destroyed by heat and removed, whereby a ceramic negative pattern is formed. The spaces previously occupied by the material of the positive pattern, i.e. of the natural or artificial sponge, are then filled by a castable or extractable metal and the ceramic material of the negative pattern is subsequently removed again. A disadvantage of this process consists in the fact that the structure of the positive pattern and thus the structure of the finished metal implant cannot be controllably adjusted but that the structure has to be accepted according to the nature of the sponges, whether natural or artificial. A further disadvantage of this process consists in the fact that it is complicated and two shaped bodies, i.e. initially a positive pattern and subsequently a negative pattern, are required in order to ultimately create a three-dimensional framework.

In DE-A-29 10 627, it is proposed to form a dimensionally stable network composed of threads or fibers of plastic or metal and to use this as an implant. This proposal is difficult to realize, however, since the network is very difficult and expensive to produce and hardly succeeds in reproducibly ensuring the dimensional stability and guaranteeing an appropriate load bearing capacity of the implant.

The object underlying the invention is thus to provide a material and a process for its preparation which enable a three-dimensional framework to be adjusted exactly according to the respective needs with respect to the porosity of the material and the thickness of the supporting structures as well as with respect to the dimensional stability and other desired properties such as solubility and absorbability.

This object is achieved by the present invention according to the patent claims. The invention thus solves an old problem in the preparation of materials which is of great importance for medicine, namely the preparation of continuously porous frameworks with an adjustable porosity and an adjustable strength as well as properties adapted to the respective needs, such as solubility and absorbability. In each case a negative pattern of the finished material is preferably used as a starting material.

The invention is based on the idea of using individual shaped bodies connected to one another, e.g. in the form of a dense packing or a conglomerate, as space retainers for the cavity structure and to create a three-dimensional framework of supporting structures, preferably of a castable material, around the easily removable, for example easily soluble or easily meltable shaped bodies. Subsequently, the shaped bodies can be removed again, either physically or chemically, preferably by applying the principle of water-solubility or of fusibility, or by applying heat. According to the invention, the individual shaped bodies themselves can also be produced according to the principles of a positive/negative pattern.

In other words, the invention is based in principle on the finding that by means of shaped bodies having a predetermined configuration, for example spherical or granular shaped bodies which are connected to one another at their points of contact to give a three-dimensional structure in the form of a conglomerate, a continuous beamlike or trabecular cavity structure is formed. This cavity structure is subsequently filled with another material. The spacial structure of the material used for filling represents the "positive pattern" relative to the "negative pattern" formed by the conglomerate of shaped bodies and is freely adjustable by suitable choice of the structure of the negative pattern. The composite body obtained after filling can subsequently be freed from the shaped bodies which form an inlet. By removing the shaped bodies a continuously porous material is obtained. The porosity of the material is reproducibly adjustable by suitable selection of the size, size distribution and bulk density of the shaped bodies as well as the nature of their connection with one another. The finished material is mechanically resistant and can have any external form.

The material according to the invention differs from the materials prepared by conventional processes, for example in dentistry, in that the porosity and the strength of the trabecular supporting structures as well as the stability can be adjusted exactly.

According to the invention, ceramic or ceramic composite materials of high density can be prepared as positive and as negative shaped bodies by sintering techniques. According to the invention, high-strength materials in the form of metal trabeculae with continuous porosity, i.e. having cavities connected to one another, can also be prepared with castable metals or metal composite materials. Such materials are of great interest for technology.

The material according to the invention can be used in particular in medicine and here particularly for the preparation of implants or as an active substance carrier in so-called drug-delivery systems. However, the material according to the invention can also be used as a carrier of all those active substances which can be applied onto surfaces, including, for example, the bone morphogenetic protein or certain growth factors.

It has been shown that specific bone ingrowth occurs very rapidly along the preferably coated surfaces of the predeterninedly adjustable cavity structure. If the material according to the invention is used as an implant the bone ingrowth can penetrate the entire implant irrespective of the biomechanical load.

The materials according to the invention can also be used in filter technology since any desired porosity can be adjusted and any actively absorbable material can be used in combination with any desired porosity. With the material according to the invention a filter can be produced wherein a macroscopically largepore filter system can be combined with a microporous filter system.

In principle, any materials can be made into the negative or positive pattern by combining for example water-soluble or acid-soluble shaped bodies with meltable materials or watersoluble or acid-soluble shaped bodies with sinterable, castable material composites or plastics processable by injection molding, or castable metals, metal alloys or metal composite materials processable for example by centrifugal casting or injection molding, in such a manner that in each case one type of shaped body can be removed either physically or chemically or otherwise, and the three dimensional framework remains as a supporting structure. The supporting structure can subsequently be strengthened, surface-treated or mechanically refined by physical or chemical methods.

The shaped bodies and the supporting structure which preferably consists of a castable material can also be further processed together, for example mechanically, and only subsequently separated physically or chemically. The resultant three-dimensional frameworks can temporarily serve as shaped bodies for negative patterns so that both the three-dimensional framework with continuous porosity and the packing or the conglomerate of shaped bodies which are connected to one another and preferably spherical can be used reciprocally as a pattern. In this way, all possible materials, combinations of materials and composite materials can be processed to the material according to the invention.

The material for the three-dimensional framework is preferably castable or extrudable, for example by injection molding. Should the material be used as an implant, the three-dimensional framework of the material according to the invention preferably consists of a polyacrylate based or polymethacrylate based polymer, a copolymer of an acrylate and a methacrylate, a mixture of these or of another body-compatible plastic. The three-dimensional framework can also consist of an absorbable polyamino acid, a polylactate, a polyglycolate, a mixture of various polyamino acids or of another material which is soluble and/or absorbable in the body. Silicone, a caoutchouc derivative or a related rubber based polymer is preferred as the material for the three-dimensional framework if the material is used as a filter, for example as a nose filter.

The shaped bodies serving as space retainers for the cavity system of the material are preferably in the form of spheres or uniform geometrical bodies, for example polygons, although granular material can also be used as the shaped bodies. The material of the shaped bodies is preferably easily soluble, e.g. water-soluble or acid-soluble, or easily meltable. Particularly preferred are shaped bodies of a water-soluble material, for example sugar, which can first be adhered together in steam in order to form a conglomerate of shaped bodies and washed out after formation and curing of the three-dimensional framework, for example in a water bath or a washing machine.

The material for the shaped bodies can be an inorganic or ceramic material, for example tricalcium phosphate, a hydroxylapatite, a mixture of both or another calcium compound which is either easily or not easily absorbable, in particular if the material is used for an implant. Acid-soluble ceramic materials are preferred.

Since the size, the bulk density and the nature of the mutual connection of the shaped bodies serving as space retainers for the cavity system of the material can be freely chosen, the porosity of the cavity system of the finished material is also freely adjustable. For example, spherical shaped bodies can be used if a cavity system is sought with essentially spherical cavities connected to one another. If a cavity system with cavities of different sizes is sought, shaped bodies of different sizes and/or shapes can be mixed with one another. The total porosity of the finished material is controllably adjustable by adjusting, varying and combining the shape and/or the bulk density of the shaped bodies and/or the choice of the method by which the shaped bodies are connected to each other to form a conglomerate. According to the invention, the form and arrangement of the trabeculae of the three-dimensional framework is likewise predeterminable and controllably adjustable according to the purpose of use.

The shaped bodies can, for example, be connected to one another by sintering techniques. The preferred size of the shaped bodies is between approximately 0.5 and 5 mm, more preferably up to 3 mm, in particularly if the material is used as an implant or a filter.

A further variation of the desired properties of the finished material is also made possible by compressing the three-dimensional framework together with the shaped bodies, for example by HIP process (high isostatic pressing).

The material can also additionally contain filler particles, for example tricalcium phosphate or hydroxylapatite or a mixture of these with a content of 1 to 95%, preferably 1 to 80%, and with a particle size of 50 to 300 $\mu$m, preferably up to 250 $\mu$m, and a pore volume of 0.1 ml/g to 0.8 ml/g.

Depending on the intended use of the material, various active substances can be added to it. For example, the material for the three-dimensional framework can contain 0.01% to 10% of an active substance which can be sustainedly released from the material. Antibiotics, an active substance which induces bone growth, a growth factor or another chemotactically or hormonally active factor which induces ingrowth of the vessels or directly stimulates the osteoblasts can be used, for example, if the material is used as an implant. If the material is used as a filter the threedimensional framework can be treated with activated carbon or another filler which strongly absorbs gas and/or liquid, for example in a concentration of between 5 and 80% by weight.

The external form of the material can be freely chosen and depends on the respective purpose of use.

EXAMPLES

Example 1

Preparation of a Porous Implant with High Mechanical Strength

Ceramic spheres with a diameter of between 0.5 and 3 mm are sintered together in a sintering furnace and bonded at their points of contact into a conglomerate in the form of a porous body which serves as a negative pattern. The pores connected with one another or interconnected (cavities) of the conglomerate are filled out with a castable metal by centrifugal casting. The resultant composite material of ceramic and metal is subsequently very highly compressed by a so-called HIP process. The ceramic is then removed again by a chemical method, for example using acid, leaving a material of a three-dimensional metal framework with supporting trabecular structures and an interconnected pore system which is usable for example as an implant.

Example 2
Preparation of a High-Strength Ceramic Implant Body

Metal spheres between 0.5 and 3 mm in size are used as shaped bodies and welded or connected to one another by means of heat or spot conglutination, so that a continuously trabecular system of cavities is formed around the spheres. These very solid shaped bodies are subsequently cast-in with a ceramic mass by centrifugal casting. The resultant composite material is then highly compressed by a HIP process. The metal spheres are subsequently removed electrolytically. The remaining three-dimensional ceramic framework is further strengthened by sintering techniques. In this manner, a high-strength ceramic implant body with a three-dimensional trabecular structure is produced. The pores of the continuous cavity system are adjustable by suitable choice of the size of the metal spheres serving as space retainers.

Example 3
Preparation of an Efficient Filter

Sugar spheres between 0.5 and 3 mm in size are poured loose and then rapidly adhered to one another in steam under vacuum. The conglomerate is subsequently dried and poured in with a castable silicone mixture to which up to 80% activated carbon can be added. After curing the silicone the sugar is subsequently removed again in water, for example in a washing machine. A three-dimensional filter body of silicone of a trabecular framework with a high actively absorbing surface is obtained. The pore system of the filter body is adjustable by suitable choice of the size and the size distribution of the sugar spheres. The filter can be very effectively used for example as a nose filter in the vestibule of the nose for preventing contamination of the respiratory system. The shape of the filter is preferably adapted to the shape of the vestibule of the nose.

Example 4
Preparation of a Composite Material

Sugar spheres 0.5 to 3 mm in size are poured loosely into a mold and steam is subsequently passed through under vacuum and the sugar spheres adhere to one another. After subsequent drying the resultant mass (conglomerate) is castin with a fluid PMMA based bone cement or extruded by injection molding. After curing the bone cement or the heat-melted plastic the sugar is washed out, for example in a washing machine. The finished material in the form of a porous body has a uniform three-dimensional trabecular structure and can be inserted in the form of a cylinder as a central medullary implant. This implant can give bone screws a firm hold in an osteoporotic, biomechanically very weakened bone and can thus lead to anatomically exact reposition, for example in the case of several fragments and epiphyseal fractures. The implant produced using the material of the invention is also mechanically workable and can be completely penetrated by bone. As stated above, the material is usable for example for anchoring bone screws in the case of so-called osteosyntheses associated with bone cement or as a plug, i.e. as a so-called medullary stopper on cemented prosthesis components.

Example 5
Preparation of an Implant Body Usable as a Prosthesis Shaft for a Femur Component of a Hip-Joint Replacement Prosthesis Ceramic spheres between 0.5 and 1.5 mm in size are poured loosely into an anatomically formed first mold and sintered together in a sintering furnace. The resultant body (conglomerate) of sintered material is subsequently sunk in a similarly formed second mold, which is, however, approximately 3 to 4 mm larger than the first mold in the form of a shell, so that a uniform gap remains around the sintered body. This gap is filled with ceramic spheres 1 to 3 mm in size. The filled second mold is subsequently sintered in a sintering furnace so that a composite body of sintered spheres is formed out of the two different sphere components. This composite body as a pattern is cast-in with a castable metal alloy by centrifugal casting and subsequently compressed by a HIP process such that a high-strength metal ceramic composite body is formed. Subsequently, the large part of the ceramic is removed again, preferably chemically, except for a surface coating of the metal. In this manner, a high-strength, completely porous metal body is formed which has in its surface region different mechanical properties compared to the more massive inner portion with denser structures. This surface represents the interface to the bone if the metal body is used as an implant or prosthesis. Such a layering can also be repeatedly arranged in axial direction so that all in all any desired prosthesis shaft configuration can be mechanically adjusted and reproducibly manufactured. The optimum prosthesis shaft configuration can be calculated for example by a finite element method. Thus, implant bodies or prostheses of very sophisticated design can also be specifically produced with any continuous internal cavity system.

Although the present invention has been described with reference to preferred embodiments, workers skilled in the art will recognize that changes may be made in form and detail without departing from the spirit and scope of the invention.

I claim:

1. A process for preparing a homogenous material, said process comprising the steps of:
   connecting essentially spherical-shaped bodies at their points of contact to form a three-dimensional shaped body conglomerate;
   forming a three-dimensional framework by casting or injecting a generally incompressible liquid material different from the shaped bodies around said connected shaped bodies, the material of the framework being selected from a group consisting of polymers, ceramics and metals;
   compressing the three-dimensional framework together with the shaped bodies; and
   after at least partial hardening of the three-dimensional framework, removing the connected shaped bodies so that merely the polymer, ceramic or metallic three-dimensional framework remains in the form of the homogenous material.

2. The process according to claim 1, wherein the shaped bodies are chemically or physically bonded to one another.

3. The process according to claim 1, wherein the shaped bodies are washed out of the framework with a liquid after the framework is formed.

4. The process according to claim 1, wherein the shaped bodies are connected to one another by sintering techniques.

5. The process according to claim 1, wherein the three-dimensional framework consists of metal and the shaped bodies consist of ceramic.

6. A process for preparing a material comprising the steps of:
   forming a three-dimensional packing or a conglomerate of water-soluble shaped bodies which are connected to one another;
   forming a three-dimensional framework of a liquid wax or a liquid polymer around the connected water-soluble shaped bodies;

compressing the three-dimensional framework together with the shaped bodies;

curing the framework of the wax or the liquid polymer into a solid;

removing the water-soluble shaped bodies to form a continuous cavity system having pore sizes between 0.2 and 5 mm;

filling the pores of the continuous cavity system with a ceramic mass; and removing the framework of the wax or the polymer by applying heat.

7. The process according to claim 6, wherein the pore sizes are less than 3 mm.

8. The process according to claim 6, wherein ceramic spheres are formed in the pores of the cavity system.

9. The process according to claim 8, wherein the ceramic spheres are formed by applying heat or are welded together by sintering techniques to form solid bodies of spherical conglomerates.

10. The process according to claim 6 wherein the shaped bodies are chemically or physically connected to each other and are removed chemically or physically after the framework has been formed.

11. The process according to claim 1, wherein the three-dimensional framework is selected from a group consisting of an acrylate based polymer, a polymethacrylate based polymer, a copolymer of an acrylate and methacrylate, and of a mixture of an acrylate based polymer, a polymethacrylate polymer and a copolymer of acrylate and methacrylate.

12. The process according to claim 1, wherein the three-dimensional framework is a material which is soluble or absorbable in the body.

13. The process according to claim 1, wherein the three-dimensional framework is selected from a group consisting of a silicone and a caoutchouc derivative.

14. The process according to claim 6, wherein the material of the three-dimensional framework is cast around the connected shaped bodies.

15. The process according to claim 6, wherein the shaped bodies are of sugar, and are connected together by vacuum pressing steam through the shaped bodies.

16. The process according to claim 1, wherein the shaped bodies consist of a ceramic material selected from a group consisting of tricalcium phosphate, a hydroxylapatite, a mixture of tricalcium phosphate and a hydroxylapatite.

17. The process according to claim 1, wherein the shaped bodies are between 0.2 mm and 5 mm in size.

18. The process according to claim 1, wherein a mixture of shaped bodies of varying size is used.

19. The process according to claim 1, wherein the framework further includes 0.01 to 10% of an active substance which is protractedly releasable from the material.

20. The process according to claim 19, wherein the active substance is selected from a group consisting of gentamicin, clindamicin, a gyrase inhibitor, and a combination of two or more different antibiotics.

21. The process according to claim 19, wherein the active substance is a bone growth inducing active substance which induces ingrowth of human or animal vessels or directly stimulates the osteoblasts of a bone.

22. The process according to claim 1, wherein the material of the framework additionally comprises a filler.

23. The process according to claim 22, wherein the filler consists of filler particles with a particle size of 50 to 300 mm and a pore volume of 0.1 ml/g to 0.8 ml/g, and wherein 1 to 95% of the filler particles are selected from a group consisting of tricalcium phosphate, hydroxylapatite, and a mixture of tricalcium phosphate and hydroxylapatite.

24. The process according to claim 22, wherein the filler is selected from a group consisting of a gas-absorbing material, a liquid-absorbing material and a combination of a gas-absorbing material and a liquid-absorbing material.

25. The process according to claim 24, wherein the filler has a concentration of between 5 and 80% by weight.

26. A material prepared by the process of claim 6.

27. The process according to claim 1, further comprising shaping the three-dimensional framework in the form of an implant.

28. The process according to claim 1, further comprising shaping the three-dimensional framework in the form of a plug or medullary stopper.

29. The process according to claim 1, further comprising shaping the three-dimensional framework in the form of a filter.

30. The process of claim 1, wherein the shaped bodies are water-soluble, and wherein the shaped bodies are connected by vacuum pressing steam through the shaped bodies.

31. The process of claim 1, wherein the compression step is performed by high isostatic pressing.

32. The process according to claim 1, wherein the material of the framework is acrylate, and wherein the shaped bodies are sugar.

* * * * *